United States Patent [19]
Yang et al.

[11] Patent Number: 5,817,624
[45] Date of Patent: Oct. 6, 1998

[54] PERMEATION ENHANCER COMPOSITIONS FOR INCREASED ABSORPTION OF THERAPEUTIC PROTEINS THROUGH THE COLONIC MEMBRANE

[75] Inventors: Heechung Yang, Palo Alto; Robert E. Myrback, Milpitas, both of Calif.; Deborah A. Fox, Oakton, Va.; Vu Anh Nguyen, San Jose, Calif.

[73] Assignee: Alza Corporation, Palo Alto, Calif.

[21] Appl. No.: 465,661

[22] Filed: Jun. 5, 1995

[51] Int. Cl.$^6$ .......................... A61K 38/27; A61K 38/28; A61K 31/04

[52] U.S. Cl. ................. 514/3; 514/12; 514/730; 514/806

[58] Field of Search ................. 514/3, 12, 730, 514/806

[56] References Cited

U.S. PATENT DOCUMENTS 5,424,289  6/1995  Yang et al. ............................. 514/12

FOREIGN PATENT DOCUMENTS 0037943  10/1981  European Pat. Off. ......... A61K 9/02
0177342  4/1986  European Pat. Off. ....... A61K 37/36
0225189  6/1987  European Pat. Off. ......... A61K 9/48

OTHER PUBLICATIONS

Nishinata et al., Biochem. et Biophysica Acta vol. 775 (1984) pp. 269–271.

Goodman & Gilman's "The Pharmacological Basis of Therapeutics" 6th Ed. (MacMillan Publishing Co. Inc 1980) pp. 5–7.

Chemial Abstract, vol. 106, No. 8, 23 Feb. 1987, Columbus, Ohio, US; Abstract No. 55786.

Int. J. Pharm., vol. 34, No. 1–2, 1986, pp. 35–43; J.A. Moore et al., "Absorption Enhancement of Growth Hormone from the Gastrointestinal Tract of Rats".

*Primary Examiner*—Cecilia J. Tsang
*Assistant Examiner*—Bennett Celsa
*Attorney, Agent, or Firm*—John A. Dhuey; Steven F. Stone

[57] ABSTRACT

The present invention is directed to a pharmaceutical formulation of a therapeutic polypeptide together with a permeation-enhancing mixture of sodium 3-nitrobenzoate and an oil to provide enhanced absorption of the polypeptide through the wall of the gastrointestinal tract, and particularly of the colon, after oral administration.

16 Claims, 1 Drawing Sheet

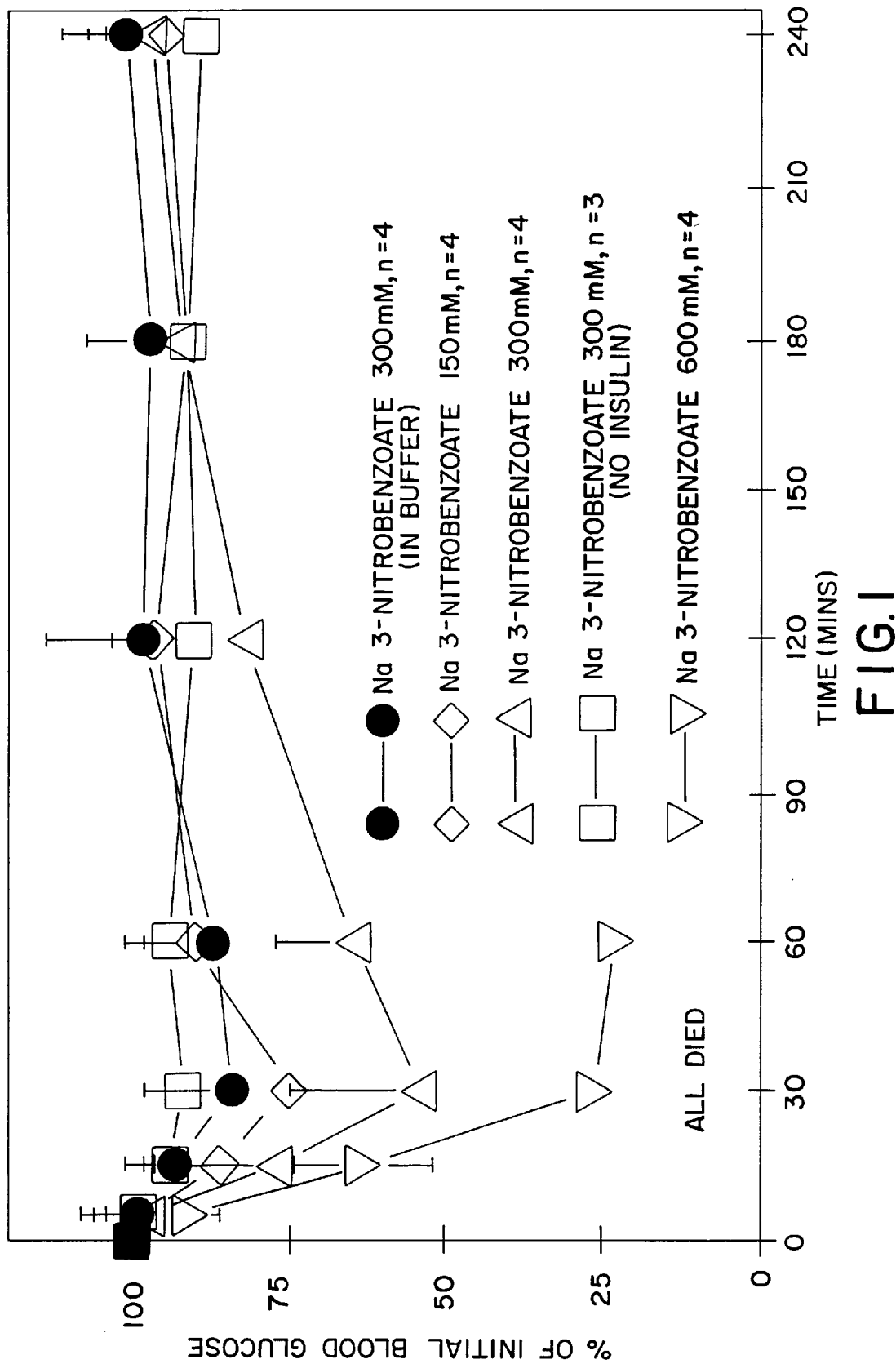

PERMEATION ENHANCER COMPOSITIONS FOR INCREASED ABSORPTION OF THERAPEUTIC PROTEINS THROUGH THE COLONIC MEMBRANE

FIELD OF THE INVENTION

The present invention relates to permeation enhancer compositions for delivery of polypeptides through the colonic membrane. More particularly, the invention relates to permeation enhancer compositions comprising sodium 3-nitrobenzoate which provide for improved absorption of polypeptides through the wall of the gastrointestinal tract after oral administration.

BACKGROUND OF THE INVENTION

The conventional route of therapy involving protein or peptide drugs is via parenteral administration (i.e., by injection). This is primarily due to the lack of absorption of such drugs through the gastrointestinal tract. However, injections are painful and sometimes difficult to administer relative to other dosage forms. Further, patient compliance is problematic where these drugs may require frequent administration, especially to juvenile or geriatric patients. Accordingly, oral delivery is preferable to injections for patient acceptance since it is less painful and more convenient. However, a number of problems are associated with oral delivery of therapeutic polypeptides through the gastrointestinal (GI) tract. These include low pH in the stomach, proteolytic degradation of the drug in the small intestine, low absorption through the intestinal membrane, and limited stability of polypeptide formulations, especially as aqueous solutions. These are all potential barriers to absorption of polypeptides following oral administration.

Recent efforts to deliver polypeptides orally have focused on the use of absorption enhancers. This has led to the discovery that a suspension of sodium salicylate in an excess of an oil can enhance the absorption of human growth hormone from the GI tract (EP publication 177,342; Moore et al., Internat. J. Pharma. 34: 35(1986)).

SUMMARY OF THE INVENTION

Surprisingly, it has now been found that sodium 3-nitrobenzoate also acts as a permeation enhancer for the delivery of a therapeutic protein/peptide formulation. Accordingly, in one aspect, the present invention is directed to a pharmaceutical formulation of a therapeutically effective polypeptide together with a permeation-enhancing amount of sodium 3-nitrobenzoate and an oil to provide enhanced absorption of the polypeptide through the wall of the gastrointestinal tract after oral administration.

In another aspect, the invention is directed to oral dosage forms comprising a therapeutically effective polypeptide, a permeation-enhancing amount of sodium 3-nitrobenzoate and an oil. In yet another aspect, the invention is directed to a method for delivering a polypeptide through the colonic membrane by administering a therapeutically effective amount of the polypeptide with a penetration enhancing amount of sodium 3-nitrobenzoate and an oil.

BRIEF DESCRIPTION OF THE DRAWING

FIG. 1 is a graph showing the comparative decrease in the blood glucose levels of fasted anesthetized male rats following administration of insulin according to this invention.

DETAILED DESCRIPTION OF THE INVENTION

The present invention is applicable to the oral administration of therapeutic proteins and polypeptides. The invention surprisingly provides greatly increased absorption through the GI tract of the proteins/peptides as compared to that of the proteins/peptides alone. The invention is useful in both human and veterinary therapy and treatment. As used herein and in the appended claims, the term "polypeptide" encompasses proteins and peptides as well as polypeptides within its scope.

The present invention is particularly useful in the administration of polypeptides, including proteins, such as, but not limited to, vaccines, antibodies, antigens, insulin, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors, fertility promoters, growth factors, human pancreas hormone releasing factor, human tissue plasminogen activator, human tumor necrosis factor, and the like, and structurally similar bioactive equivalents thereof. By "structurally similar bioactive equivalent" is meant a polypeptide with an amino acid sequence which, although not identical to that of the naturally occurring peptide, is sufficiently similar in structure to produce substantially equivalent therapeutic effects on the subject to that produced by the natural peptide itself. As used herein and in the appended claims, the terms "protein", "peptide" and "polypeptide" refer to both the naturally occurring chemical entities and the structurally similar bioactive equivalents thereof. These polypeptides may be non-lyophilized.

Unexpectedly, it has been found that an oral dosage form of a therapeutic polypeptide can be formulated with sodium 3-nitrobenzoate and an oil to provide substantially increased absorption of the peptide through the gastrointestinal (GI) tract and particularly through the colon or ileum.

The oil may be chosen from any pharmaceutically acceptable oil including, but not limited to, mineral oil, silicone oil, peanut oil, coconut oil, corn oil, sesame oil, olive oil, fatty acids, vitamin E, and the like. Presently preferred are peanut oil and corn oil.

The "penetration-enhancing amount" of sodium 3-nitrobenzoate present in the pharmaceutical formulation is the amount required to substantially increase the absorption of active agent through the gastrointestinal tract. The penetration-enhancing amount of sodium 3-nitrobenzoate is from about 1% (w/w) to about 50% (w/w), preferably from about 10% (w/w) to about 40% (w/w).

The amount of oil in the pharmaceutical formulation is from about 50% (w/w) to about 99% (w/w), preferably from about 60% (w/w) to about 90% (w/w).

The amount of therapeutic polypeptide will vary widely, depending on various factors such as the particular peptide to be delivered, the indication to be treated, the individual patient, and the like. The amount will be a therapeutically effective amount, that is, an amount which will provide a therapeutic effect, to be determined in accordance with well-established medical practice.

Oral administration of the polypeptide may be problematic where a low gastric pH level and the presence of proteolytic enzymes in the upper GI tract inactivate the peptide before it can be absorbed by the intestinal mucosa. This problem may be solved by the use of enteric coatings where the oral dosage form is a tablet or a capsule. Enteric coatings will remain intact in the stomach but will rapidly dissolve once the tablet or capsules arrive at the small intestine. The drug will thereafter be released at a site downstream of the stomach in the intestine (eg, the ileum and colon). Enteric coatings are well known in the art and are discussed in, for example, *Remington's Pharmaceutical Sciences*, Mack Publishing Co., Easton, Pa.; and *Polymers for Controlled Drug Delivery*, Chapter 3, CRC Press, 1991. Alternatively, a controlled release oral delivery vessel designed to release a drug after a predetermined period of time, and thus after the vessel has passed into the ileum or colon, can be used to deliver the formulation of the present invention. Such vessels include the CHRONSET® delivery device (ALZA Corporation, Palo Alto, Calif.) and the Pulsincap™ delivery device (R.P. Scherer Co.).

To prepare the pharmaceutical formulation of the present invention, the polypeptide and the sodium 3-nitrobenzoate are suspended in oil and mixed before being placed into a capsule formed of gelatin or the like and coated with an enteric compound, or placed into a controlled release delivery device such as the CHRONSET® or the Pulsincap™.

The following examples are illustrations of the present invention, and are intended neither to define nor to limit the scope of the invention in any manner.

EXAMPLE 1

An animal model commonly known as the "intracolonic ligated model" was employed for testing formulations. Surgical preparation of a fasted anesthetized 0.3–0.5 kg Sprague-Dawley male rats proceeded as follows. A segment of proximal colon was isolated and the colon was flushed of fecal materials. The segment was ligated at both ends while a catheter was placed in the lumen and exteriorized above the skin for delivery of test formulation. The colonic contents were flushed out and the colon was returned to the abdomen of the animal. Depending on the experimental set up, the test formulation was added after the segment was filled with 1 mL/kg of 20 mM sodium phosphate buffer, pH 7.4, to more accurately simulate the actual colon environment in a clinical situation.

Rats were allowed to equilibrate for approximately 1 hour after surgical preparation and prior to exposure to each test formulation. Immediately prior to test solution administration, a 0.3–0.5 mL blood sample was taken from the jugular catheter of the rats and analyzed for glucose content using an Ames GlucometerM® blood glucose meter utilizing Glucostix® reagent strips. Withdrawn blood was replaced with an equal volume of heparinized Ringer's. Sodium bovine insulin was formulated to be delivered at a dose of 0.5 mg/kg body weight. Initially, all candidate enhancers were tested at a concentration of 300 mM. Those compounds demonstrating enhancer capabilities were evaluated at higher and lower concentrations in order to develop dose response relationships. The solutes ( enhancer and insulin) were suspended in 1 mL peanut oil (except where noted) and mixed using a vortex mixer. Test solutions were vortexed immediately prior to aspiration into individual delivery syringes.

After determination of baseline blood glucose levels, the test solution was administered as an intracolonic bolus and delivered at 1 ml/kg adjusting for either the 100 μl or 250 μl dead volume of the colonic catheter. Blood samples obtained from the jugular catheter were taken at 0, 5, 15, 30, 60, 120, 180 and 240 minutes and analyzed for blood glucose concentration. At the end of the 4 hour test period, the rats were euthanized with an overdose of pentobarbital. Colonic segments from each rat were excised and opened longitudinally along the anti-mesenteric border. Each segment was observed macroscopically for irritation and any abnormality noted. The excised colons were placed on graph paper and measured to approximate colonic surface area. Blood glucose dynamics are reported as the percent change from initial blood glucose levels.

The maximum percent decrease in blood glucose levels for each compound tested during the first 60 minutes of test solution exposure to the colon is shown in Table I.

TABLE I

| Enhancer/Salicylate Derivative | Concentration mM | % Maximum Decrease 0–60 mins* |
|---|---|---|
| Asp—Phe methyl ester (Aspartame) | 300 | 8 |
| Benzoic acid | 300 | 9 |
| Benzoic acid, Na salt | 300 | 0 |
| 5-Amino salicylic acid | 300 | 0 |
| 5-Amino salicylic acid, Na salt | 100 | 13 |
| 5-Amino salicylic acid, Na salt | 300 | 13 |
| 2-Nitrobenzoic acid | 300 | 8 |
| 3-Nitrobenzoic acid | 300 | 0 |
| 3-Nitrobenzoic acid, Na salt | 150 | 25 |
| 3-Nitrobenzoic acid, Na salt | 300 | 46 |
| 3-Nitrobenzoic acid, Na salt (No insulin) | 300 | 8 |
| 3-Nitrobenzoic acid, Na salt | 600 | 77** |
| 4-Nitrobenzoic acid | 300 | 2 |
| 2-Aminobenzoic acid (anthranilic acid) | 300 | 0 |
| 4-Amino salicylic acid | 300 | 3 |
| 4-Amino salicylic acid, Na salt | 300 | 10 |
| 5-Methoxysalicylic acid (Aldrich) | 100 | 5 |
| 5-Methoxysalicylic acid (Aldrich) | 1000 | 4 |
| 5-Methoxysalicylic acid, Na salt | 300 | 9 |
| 2,5-Dihydroxybenzoic (Gentisic acid) | 300 | 16 |
| 2,5-Dihydroxybenzoic acid, Na salt | 300 | 1 |
| 2,5-Dihydroxybenzoic acid, Na salt | 300 | 9 |
| 2-Hydroxy-5-Nitrobenzoic acid | 300 | 4 |
| Na Salicylate | 150 | 19 |
| Na Salicylate | 300 | 64 |
| Na Salicylate | 600 | 79** |
| Na Salicylate (No insulin) | 600 | 13 |
| Na Salicylate | 250 | 45 |
| Na Salicylate (½ mL peanut oil) | 250 | 43 |
| Na Salicylate (¼ mL peanut oil) | 250 | 53 |
| Na Salicylate (⅛ mL peanut oil) | 250 | 58*** |
| NaCl | 300 | 2 |
| Na Salicylate (300 mM) + CaCl$_2$ (150 mM) | | 29 |
| Na Salicylate (300 mM) + Amiloride 2.7 mg/kg iv | | 42 |
| Na Salicylate (300 mM) + Amiloride 2.7 mg/kg ic | | 48 |

*n = 3–4
**4/4 died
***2/4 died

Only sodium salicylate and sodium 3-nitrobenzoate at concentrations of 300 mM in combination with sodium bovine insulin (0.5 mg/kg) and peanut oil caused a significant decrease in fasting blood glucose levels. No other salicylate derivative caused a significant decrease in blood glucose levels from pre-exposure levels.

EXAMPLE 2

Rats were prepared as described in EXAMPLE 1. The rats were given 150 to 600 mM of sodium 3-nitrobenzoate. At the 300 mM concentration level, the formulations were given according to the invention (ie, with insulin, oil, and sodium 3-nitrobenzoate) without insulin (ie, oil and 3-nitrobenzoate only) and without oil (ie, with insulin, sodium 3-nitrobenzoate and buffer). FIG. 1 depicts the dose dependent decrease of blood glucose levels at increasing concentrations of enhancer. The open symbols denote the formulations delivered in oil whereas the closed symbol denotes the formulation without oil. All rats in the treatment groups receiving 600 mM sodium 3-nitrobenzoate in combination with insulin and peanut oil died due to low blood glucose levels. At a concentration of 300 mM, both sodium salicylate and sodium 3-nitrobenzoate formulated without insulin had no effect on blood glucose levels over a 4 hour period. Further, sodium 3-nitrobenzoate is only active in the presence of oil.

While this invention has been described with respect to certain specific embodiments thereof, it should not be construed as being limited thereto. Numerous modifications and substitutions will suggest themselves to workers skilled in the art and may be made without departing from the scope of this invention, which is limited only by the following claims.

What is claimed is:

1. A pharmaceutical formulation for the oral delivery of a therapeutic polypeptide which comprises a therapeutically effective amount of a polypeptide selected from the group consisting of growth hormone and insulin, a penetration enhancing amount of sodium 3-nitrobenzoate, and a pharmaceutically acceptable oil.

2. A pharmaceutical formulation according to claim 1 wherein the oil is present in an amount of 50–99% (w/w).

3. A pharmaceutical formulation according to claim 1 wherein the oil is selected from the group consisting of mineral oil, silicone oil, peanut oil, coconut oil, corn oil, sesame oil, olive oil, fatty acids, and vitamin E.

4. A pharmaceutical formulation according to claim 1 wherein the oil is selected from peanut oil and corn oil.

5. A pharmaceutical formulation according to claim 1 wherein the polypeptide is insulin.

6. A pharmaceutical formulation according to claim 5 wherein the sodium 3-nitrobenzoate is present in an amount of 1–50% (w/w).

7. A ph armaceutical formulation according to claim 1 wherein the polypeptide is human growth hormone.

8. A pharmaceutical formulation according to claim 7 wherein the sodium 3-nitrobenzoate is present in an amount of 1–50% (w/w).

9. An oral dosage form comprising a therapeutically effective polypeptide selected from the group consisting of growth hormone and insulin, a penetration enhancing amount of sodium 3-nitrobenzoate, and a pharmaceutically acceptable oil.

10. The oral dosage form of claim 9 further comprising an enteric coating.

11. The oral dosage form of claim 9 that is selected from a capsule and a controlled release delivery device.

12. A method for delivering a polypeptide through the colonic membrane, the method comprising orally administering a pharmaceutical formulation which comprises a therapeutically effective amount of a polypeptide selected from the group consisting of growth hormone and insulin, a penetration enhancing amount of sodium 3-nitrobenzoate, and a pharmaceutically acceptable oil.

13. A method according to claim 12 wherein the polypeptide is human growth hormone and the oil is selected from the group consisting of mineral oil, silicone oil, peanut oil, coconut oil, corn oil, sesame oil, olive oil, fatty acids, and vitamin E.

14. The method of claim 12 wherein the polypeptide is insulin.

15. The method of claim 12 wherein the polypeptide is human growth hormone.

16. A composition of matter comprising sodium 3-nitrobenzoate and a pharmaceutically acceptable oil.

* * * * *